(12) United States Patent
Desenne et al.

(10) Patent No.: US 9,072,915 B2
(45) Date of Patent: Jul. 7, 2015

(54) COMPOSITION CONTAINING AT LEAST ONE VOLATILE LINEAR ALKANE AND AT LEAST ONE CATIONIC SURFACTANT

(75) Inventors: Patricia Desenne, Pringy (FR); Laurent Chesneau, Levallois (FR)

(73) Assignee: L'OREAL, Paris (FR)

( * ) Notice: Subject to any disclaimer, the term of this patent is extended or adjusted under 35 U.S.C. 154(b) by 267 days.

(21) Appl. No.: 12/969,980

(22) Filed: Dec. 16, 2010

(65) Prior Publication Data

US 2011/0150809 A1 Jun. 23, 2011

Related U.S. Application Data

(60) Provisional application No. 61/296,491, filed on Jan. 20, 2010.

(30) Foreign Application Priority Data

Dec. 23, 2009 (FR) ...................... 09 59549

(51) Int. Cl.
| | |
|---|---|
| A61Q 5/00 | (2006.01) |
| A61Q 5/12 | (2006.01) |
| A61K 8/31 | (2006.01) |
| A61K 8/41 | (2006.01) |
| A61K 8/42 | (2006.01) |
| A61K 8/81 | (2006.01) |

(52) U.S. Cl.
CPC ... *A61Q 5/00* (2013.01); *A61K 8/31* (2013.01); *A61K 8/41* (2013.01); *A61K 8/42* (2013.01); *A61K 8/8152* (2013.01); *A61Q 5/12* (2013.01)

(58) Field of Classification Search
None
See application file for complete search history.

(56) References Cited

U.S. PATENT DOCUMENTS

| | | | | |
|---|---|---|---|---|
| 4,387,090 A | * | 6/1983 | Bolich, Jr. | 424/70.12 |
| 8,252,271 B2 | * | 8/2012 | Singer et al. | 424/70.12 |
| 2010/0183536 A1 | * | 7/2010 | Ansmann et al. | 424/65 |

FOREIGN PATENT DOCUMENTS

WO   WO 2008/155057   * 12/2008

OTHER PUBLICATIONS

U.S. Appl. No 12/977,183, filed Dec. 23, 2010, Desenne, et al.
U.S. Appl. No 12/975,705, filed Dec. 22, 2010, Desenne, et al.
U.S. Appl. No 12/970,988, filed Dec. 17, 2010, Desenne, et al.
U.S. Appl. No 12/977,257, filed Dec. 23, 2010, Desenne, et al.
U.S. Appl. No 12/977,204, filed Dec. 23, 2010, Desenne, et al.
U.S. Appl. No 12/977,227, filed Dec. 23, 2010, Desenne, et al.
U.S. Appl. No 12/975,632, filed Dec. 22, 2010, Desenne, et al.

* cited by examiner

*Primary Examiner* — Jyothsna Venkat
(74) *Attorney, Agent, or Firm* — Oblon, McClelland, Maier & Neustadt, L.L.P.

(57) ABSTRACT

Composition containing, in a cosmetically acceptable medium, at least 2.5% by weight of one or more volatile linear alkanes relative to the total weight of the composition, and one or more cationic surfactants, where the volatile linear alkane(s)/cationic surfactant(s) weight ratio is less than or equal to 1.5. Use of this composition for the treatment of keratin materials, preferably the hair.

4 Claims, No Drawings

COMPOSITION CONTAINING AT LEAST ONE VOLATILE LINEAR ALKANE AND AT LEAST ONE CATIONIC SURFACTANT

REFERENCE TO PRIOR APPLICATIONS

This application claims priority to U.S. provisional application Ser. No. 61/296,491, filed Jan. 20, 2010; and to French patent application 09 59549, filed Dec. 23, 2009, both incorporated herein by reference.

FIELD OF THE INVENTION

The present invention relates to a composition comprising one or more volatile linear alkane(s) and one or more cationic surfactant(s), in particular proportions, to its use for the cosmetic treatment of keratin materials, preferably keratin fibres such as the hair, and to a cosmetic process for treating keratin materials using the composition.

BACKGROUND OF THE INVENTION

In the field of hair treatment, the use of volatile solvents is known in rinse-out or leave-in haircare products. They are generally used for various reasons. They especially make it possible to modify the sensory feel of a haircare product by giving it a light and non-tacky texture in the hand. They may also give it a slippery nature, which facilitates the spreading of the product onto the hair and in particular onto dry hair.

In aqueous emulsions of oil-in-water type, which may be in the form of more or less gelled creams, the addition of volatile solvents may also allow the dissolution of silicone gums, which, on account of their intrinsic viscosity, would be difficult to introduce into the compositions.

These volatile solvents, which are generally liquid fatty esters, hydrocarbon-based oils of isododecane or isohexadecane type, and/or silicone oils, may especially give rise to problems in terms of a greasy feel, lack of sheen, and stiff, hard hair.

There is thus still a need to replace these volatile solvents in order to avoid the drawbacks mentioned above.

DETAILED DESCRIPTION OF THE PREFERRED EMBODIMENTS

The inventors have now discovered, surprisingly and unexpectedly, that the combination of at least one volatile linear alkane and at least one cationic surfactant in a particular weight ratio and in particular proportions makes it possible to avoid the drawbacks mentioned above and to improve the cosmetic properties such as the smoothing, the suppleness, the disentangling, the volume especially by lifting the roots, and the tonicity of the head of hair.

In particular, the composition according to the invention makes it possible to obtain smoother, more supple hair with uniform behaviour along the length of the hair and between hairs, at the time of rinsing. On wet hair, hair that is easier to disentangle or more tonic and/or whose roots are more lifted (at the roots, the hairs are not flattened onto the scalp, but form an angle, which gives volume) is obtained. In addition, dry hair is more supple and/or has a smoother feel.

Thus, one subject of the invention is a composition comprising, preferably in a cosmetically acceptable medium:

- at least 2.5% by weight of one or more volatile linear alkanes relative to the total weight of the composition, and
- one or more cationic surfactants, the volatile linear alkane(s)/cationic surfactant(s) weight ratio being less than or equal to 1.5.

A subject of the invention is also the use of the composition for the cosmetic treatment of keratin materials, preferably keratin fibres such as the hair, especially as a rinse-out haircare product.

Another subject of the invention is a cosmetic process for treating keratin materials, preferably keratin fibres such as the hair, using the composition.

The cosmetic composition according to the invention comprises, in a cosmetically acceptable medium:

- at least 2.5% by weight of one or more volatile linear alkanes relative to the total weight of the composition, and
- one or more cationic surfactants, the weight ratio of the amount of volatile linear alkane(s) to the amount of cationic surfactant(s) being less than or equal to 1.5.

The ratio preferably ranges from 0.01 to 1.5, in particular from 0.1 to 1.4 and better still from 0.5 to 1.2.

The term "one or more volatile linear alkane(s)" means, without preference, "one or more volatile linear alkane oil(s)".

A volatile linear alkane that is suitable for use in the invention is liquid at room temperature (about 25° C.) and at atmospheric pressure (101 325 Pa or 760 mmHg).

The term "volatile linear alkane that is suitable for use in the invention" means a linear alkane that can evaporate on contact with the skin in less than one hour, at room temperature (25° C.) and atmospheric pressure (101 325 Pa), which is liquid at room temperature, especially having an evaporation rate ranging from 0.01 to 15 mg/cm2/minute, at room temperature (25° C.) and atmospheric pressure (101 325 Pa).

Preferably, the volatile linear alkane(s) that are suitable for use in the invention have an evaporation rate ranging from 0.01 to 3.5 mg/cm2/minute and better still from 0.01 to 1.5 mg/cm2/minute, at room temperature (25° C.) and atmospheric pressure (101 325 Pa).

More preferably, the volatile linear alkane(s) that are suitable for use in the invention have an evaporation rate ranging from 0.01 to 0.8 mg/cm2/minute, preferentially from 0.01 to 0.3 mg/cm2/minute and even more preferentially from 0.01 to 0.12 mg/cm2/minute, at room temperature (25° C.) and atmospheric pressure (101 325 Pa).

The evaporation rate of a volatile alkane in accordance with the invention (and more generally of a volatile solvent) may especially be evaluated by means of the protocol described in WO 06/013 413, and more particularly by means of the protocol described below.

15 g of volatile hydrocarbon-based solvent are placed in a crystallizing dish (diameter: 7 cm) placed on a balance that is in a chamber of about 0.3 m3 with regulated temperature (25° C.) and hygrometry (50% relative humidity).

The volatile hydrocarbon-based solvent is allowed to evaporate freely, without stirring it, while providing ventilation by means of a fan (Papst-Motoren, reference 8550 N, rotating at 2700 rpm) placed in a vertical position above the crystallizing dish containing the volatile hydrocarbon-based solvent, the blades being directed towards the crystallizing dish, 20 cm away from the bottom of the dish.

The mass of volatile hydrocarbon-based solvent remaining in the crystallizing dish is measured at regular time intervals.

The evaporation profile of the solvent is then obtained by plotting the curve of the amount of product evaporated (in mg/cm2) as a function of the time (in minutes).

The evaporation rate is then calculated, which corresponds to the tangent to the origin of the curve obtained. The evaporation rates are expressed as mg of volatile solvent evaporated per unit surface area (cm2) and per unit of time (minutes).

According to one preferred embodiment, the volatile linear alkane(s) that are suitable for use in the invention have a non-zero vapour pressure (also known as the saturating vapour pressure), at room temperature, in particular a vapour pressure ranging from 0.3 Pa to 6000 Pa.

Preferably, the volatile linear alkane(s) that are suitable for use in the invention have a vapour pressure ranging from 0.3 to 2000 Pa and better still from 0.3 to 1000 Pa, at room temperature (25° C.).

More preferably, the volatile linear alkane(s) that are suitable for use in the invention have a vapour pressure ranging from 0.4 to 600 Pa, preferentially from 1 to 200 Pa and even more preferentially from 3 to 60 Pa, at room temperature (25° C.).

According to one embodiment, a volatile linear alkane that is suitable for use in the invention may have a flash point that is within the range from 30 to 120° C. and more particularly from 40 to 100° C. The flash point is in particular measured according to standard ISO 3679.

According to one embodiment, the volatile linear alkane(s) that are suitable for use in the invention may be linear alkanes comprising from 7 to 15 carbon atoms, preferably from 8 to 14 carbon atoms and better still from 9 to 14 carbon atoms.

More preferably, the volatile linear alkane(s) that are suitable for use in the invention comprise from 10 to 14 carbon atoms and even more preferentially from 11 to 14 carbon atoms.

The volatile linear alkane(s) that are suitable for use in the invention may advantageously be of plant origin.

Preferably, the volatile linear alkane or the mixture of volatile linear alkanes present in the composition according to the invention comprises at least one 14C (carbon-14) carbon isotope. In particular, the 14C isotope may be present in a 14C/12C isotope ratio (by number of isotopes) of greater than or equal to $1 \times 10^{-16}$, preferably greater than or equal to $1 \times 10^{-15}$, more preferably greater than or equal to $7.5 \times 10^{-14}$ and better still greater than or equal to $1.5 \times 10^{-13}$. Preferably, the 14C/12C isotope ratio ranges from $6 \times 10^{-13}$ to $1.2 \times 10^{-12}$.

The amount of 14C isotopes in the volatile linear alkane or the mixture of volatile linear alkanes may be determined via methods known to those skilled in the art such as the Libby counting method, liquid scintillation spectrometry or accelerator mass spectrometry.

Such an alkane or mixture of alkanes may be obtained, directly or in several steps, from a plant raw material, such as an oil, a butter, a wax, etc.

As examples of alkanes that are suitable for use in the invention, mention may be made of the alkanes described in patent applications WO 2007/068 371 and WO 2008/155 059. These alkanes are obtained from fatty alcohols, which are themselves obtained from coconut oil or palm oil.

As examples of linear alkanes that are suitable for use in the invention, mention may be made of n-heptane (C7), n-octane (C8), n-nonane (C9), n-decane (C10), n-undecane (C11), n-dodecane (C12), n-tridecane (C13) and n-tetradecane (C14), and mixtures thereof. According to one particular embodiment, the volatile linear alkane is chosen from n-nonane, n-undecane, n-dodecane, n-tridecane and n-tetradecane, and mixtures thereof.

According to one preferred embodiment, mention may be made of mixtures of n-undecane (C11) and of n-tridecane (C13) obtained especially in Examples 1 and 2 of patent application WO 2008/155 059.

Mention may also be made of n-dodecane (C12) and n-tetradecane (C14) sold, respectively, under the references Parafol 12-97 and Parafol 14-97 by the company Sasol, and also mixtures thereof.

One embodiment consists in using only one volatile linear alkane.

Alternatively, a mixture of at least two different volatile linear alkanes, differing from each other by a carbon number n of at least 1, in particular differing from each other by a carbon number of 1 or 2, may be used.

According to one embodiment, a mixture of at least two different volatile linear alkanes comprising from 10 to 14 carbon atoms and differing from each other by a carbon number of at least 1 is used. Examples that may especially be mentioned include mixtures of C10/C11, C11/C12 or C12/C13 volatile linear alkanes.

According to another embodiment, a mixture of at least two different volatile linear alkanes comprising from 10 to 14 carbon atoms and differing from each other by a carbon number of at least 2 is used. Examples that may especially be mentioned include mixtures of C10/C12 or C12/C14 volatile linear alkanes, for an even carbon number n, and the C11/C13 mixture for an odd carbon number n.

According to one preferred embodiment, a mixture of at least two different volatile linear alkanes comprising from 10 to 14 carbon atoms and differing from each other by a carbon number of at least 2, and in particular a mixture of C11/C13 volatile linear alkanes or a mixture of C12/C14 volatile linear alkanes, is used.

Other mixtures combining more than two volatile linear alkanes according to the invention, for instance a mixture of at least three different volatile linear alkanes comprising from 7 to 15 carbon atoms and differing from each other by a carbon number of at least 1, may be used in the invention.

In the case of mixtures of two volatile linear alkanes, the two volatile linear alkanes preferably represent more than 95% and better still more than 99% by weight of the mixture.

According to one particular mode of the invention, in a mixture of volatile linear alkanes, the volatile linear alkane having the smaller carbon number is predominant in the mixture.

According to another mode of the invention, a mixture of volatile linear alkanes in which the volatile linear alkane having the larger carbon number is predominant in the mixture is used.

As examples of mixtures that are suitable for use in the invention, mention may be made especially of the following mixtures:

from 50% to 90% by weight, preferably from 55% to 80% by weight and more preferentially from 60% to 75% by weight of Cn volatile linear alkane with n ranging from 7 to 15, from 10% to 50% by weight, preferably from 20% to 45% by weight and preferably from 24% to 40% by weight of Cn+x volatile linear alkane with x greater than or equal to 1, preferably x=1 or x=2, with n+x between 8 and 14, relative to the total weight of alkanes in the mixture.

In particular, the mixture of volatile linear alkanes may also contain:

less than 2% by weight and preferably less than 1% by weight of branched hydrocarbons, and/or less than 2% by weight and preferably less than 1% by weight of aromatic hydrocarbons, and/or less than 2% by weight and preferably less than 1% by weight and preferentially less than 0.1% by weight of unsaturated hydrocarbons, the percentages being expressed relative to the total weight of the mixture.

More particularly, the volatile linear alkanes that are suitable for use in the invention may be used in the form of an n-undecane/n-tridecane mixture.

In particular, a mixture of volatile linear alkanes will be used comprising:

from 55% to 80% by weight and preferably from 60% to 75% by weight of C11 volatile linear alkane (n-undecane) and from 20% to 45% by weight and preferably from 24% to 40% by weight of C13 volatile linear alkane (n-tridecane), relative to the total weight of alkanes in the mixture.

According to one particular embodiment, the mixture of alkanes is an n-undecane/n-tridecane mixture. In particular, such a mixture may be obtained according to Example 1 or Example 2 of patent application WO 2008/155 059.

According to another particular embodiment, the n-dodecane sold under the reference Parafol 12-97 by Sasol is used.

According to another particular embodiment, the n-tetradecane sold under the reference Parafol 14-97 by Sasol is used.

According to yet another embodiment, a mixture of n-dodecane and n-tetradecane is used, preferably in an 85/15 ratio, such as the mixture sold under the name Vegelight 1214 by the company Biosynthis.

The composition of the invention preferably comprises from 2.5% to 90% by weight and more preferentially from 2.6% to 50% by weight of volatile linear alkane(s), in particular from 3% to 40% by weight, more particularly from 3% to 30% by weight and better still from 3% to 10% by weight of volatile linear alkane(s), relative to the total weight of the composition.

The composition according to the invention comprises one or more cationic surfactants.

The term "cationic surfactant" means a surfactant that is positively charged when it is contained in the composition according to the invention. This surfactant may bear one or more positive permanent charges or may contain one or more cationizable functions in the composition according to the invention.

As examples of cationic surfactants that may be used in the cosmetic composition, mention may be made especially of optionally polyoxyalkylenated primary, secondary or tertiary fatty amines, or salts thereof, and quaternary ammonium salts, and mixtures thereof.

The fatty amines generally comprise at least one C8-C30 hydrocarbon-based chain. Among the fatty amines that may be used according to the invention, an example that may be mentioned is stearylamidopropyldimethylamine.

Examples of quaternary ammonium salts that may especially be mentioned include:

those having the general formula (I) below:

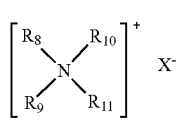

(I)

in which the radicals R8 to R11, which may be identical or different, represent a linear or branched aliphatic radical comprising from 1 to 30 carbon atoms or an aromatic radical such as aryl or alkylaryl, at least one of the radicals R8 to R11 comprising from 8 to 30 carbon atoms and preferably from 12 to 24 carbon atoms. The aliphatic radicals may comprise heteroatoms especially such as oxygen, nitrogen, sulfur and halogens.

The aliphatic radicals are chosen, for example, from alkyl, alkoxy, polyoxy(C2-C6)alkylene, alkylamide, (C12-C22) alkylamido(C2-C6)alkyl, (C12-C22)alkylacetate and hydroxyalkyl radicals, comprising from about 1 to 30 carbon atoms; X— is an anion chosen from the group of halides, phosphates, acetates, lactates, (C2-C6)alkyl sulfates, alkyl sulfonates and alkylaryl sulfonates;

quaternary ammonium salts of imidazoline, for instance those of formula (II) below:

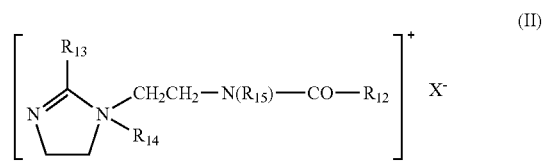

(II)

in which R12 represents an alkenyl or alkyl radical comprising from 8 to 30 carbon atoms, for example fatty acid derivatives of tallow, R13 represents a hydrogen atom, a C1-C4 alkyl radical or an alkenyl or alkyl radical comprising from 8 to 30 carbon atoms, R14 represents a C1-C4 alkyl radical, R15 represents a hydrogen atom or a C1-C4 alkyl radical, and X— is an anion chosen from the group of halides, phosphates, acetates, lactates, alkyl sulfates, alkyl sulfonates and alkylaryl sulfonates. R12 and R13 preferably denote a mixture of alkenyl or alkyl radicals comprising from 12 to 21 carbon atoms, for example fatty acid derivatives of tallow, R14 denotes a methyl radical and R15 denotes a hydrogen atom. Such a product is sold, for example, under the name Rewoquat® W75 by the company Rewo;

the diquaternary ammonium salts of formula (III):

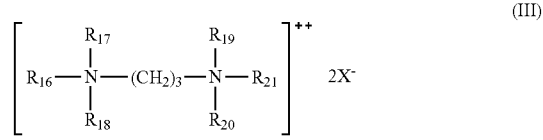

(III)

in which R16 denotes an aliphatic radical comprising from about 16 to 30 carbon atoms, R17, R18, R19, R20 and R21, which may be identical or different, are chosen from hydrogen and an alkyl radical comprising from 1 to 4 carbon atoms, and X— is an anion chosen from the group of halides, acetates, phosphates, nitrates and methyl sulfates. Such diquaternary ammonium salts especially comprise propanetallowediammonium dichloride;

quaternary ammonium salts containing at least one ester function, such as those of formula (IV) below:

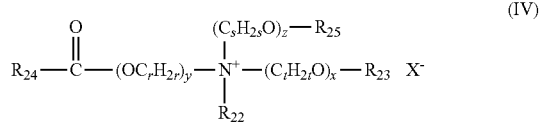

(IV)

in which:

R22 is chosen from C1-C6 alkyl radicals and C1-C6 hydroxyalkyl or dihydroxyalkyl radicals;

R23 is chosen from:
a radical

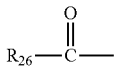

linear or branched, saturated or unsaturated C1-C22 hydrocarbon-based radicals R27,
a hydrogen atom,
R25 is chosen from:
a radical

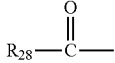

linear or branched, saturated or unsaturated C1-C6 hydrocarbon-based radicals R29,
a hydrogen atom,
R24, R26 and R28, which may be identical or different, are chosen from linear or branched, saturated or unsaturated C7-C21 hydrocarbon-based radicals;
r, s and t, which may be identical or different, are integers ranging from 2 to 6;
y is an integer ranging from 1 to 10;
x and z, which may be identical or different, are integers ranging from 0 to 10;
X— is a simple or complex, organic or mineral anion;
with the proviso that the sum x+y+z is from 1 to 15, that when x is 0, then R23 denotes R27 and that when z is 0, then R25 denotes R29.

The alkyl radicals R22 may be linear or branched, but more particularly linear.

R22 preferably denotes a methyl, ethyl, hydroxyethyl or dihydroxypropyl radical, and more particularly a methyl or ethyl radical.

Advantageously, the sum x+y+z is from 1 to 10.

When R23 is a hydrocarbon-based radical R27, it may be long and may contain from 12 to 22 carbon atoms, or may be short and may contain from 1 to 3 carbon atoms.

When R25 is a hydrocarbon-based radical R29, it preferably contains 1 to 3 carbon atoms.

Advantageously, R24, R26 and R28, which may be identical or different, are chosen from linear or branched, saturated or unsaturated C11-C21 hydrocarbon-based radicals, and more particularly from linear or branched, saturated or unsaturated C11-C21 alkyl and alkenyl radicals.

Preferably, x and z, which may be identical or different, are equal to 0 or 1.

Advantageously, y is equal to 1.

Preferably, r, s and t, which may be identical or different, are equal to 2 or 3, and even more particularly are equal to 2.

The anion X— is preferably a halide (chloride, bromide or iodide) or an alkyl sulfate, more particularly methyl sulfate. However, methanesulfonate, phosphate, nitrate, tosylate, an anion derived from an organic acid, such as acetate or lactate, or any other anion that is compatible with the ammonium containing an ester function, may be used.

The anion X— is even more particularly chloride or methyl sulfate.

Use is made more particularly in the composition according to the invention of the ammonium salts of formula (IV) in which:

R22 denotes a methyl or ethyl radical,
x and y are equal to 1;
z is equal to 0 or 1;
r, s and t are equal to 2;
R23 is chosen from:
a radical

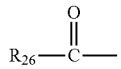

methyl, ethyl or C14-C22 hydrocarbon-based radicals,
a hydrogen atom;
R25 is chosen from:
a radical

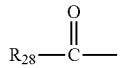

a hydrogen atom;
R24, R26 and R28, which may be identical or different, are chosen from linear or branched, saturated or unsaturated C13-C17 hydrocarbon-based radicals and preferably from linear or branched, saturated or unsaturated C13-C17 alkyl and alkenyl radicals.

The hydrocarbon-based radicals are advantageously linear. Examples that may be mentioned include the compounds of formula (IV) such as the diacyloxyethyl-dimethylammonium, diacyloxyethylhydroxyethylmethylammonium, monoacyloxyethyldihydroxyethylmethylammonium, triacyloxyethylmethylammonium and monoacyloxyethylhydroxyethyldimethylammonium salts (chloride or methyl sulfate in particular), and mixtures thereof. The acyl radicals preferably contain 14 to 18 carbon atoms and are obtained more particularly from a plant oil such as palm oil or sunflower oil. When the compound contains several acyl radicals, these radicals may be identical or different.

These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of plant or animal origin, or by transesterification of the methyl esters thereof. This esterification is followed by a quaternization using an alkylating agent such as an alkyl halide (preferably a methyl or ethyl halide), a dialkyl sulfate (preferably dimethyl or diethyl sulfate), methyl methanesulfonate, methyl para-toluenesulfonate, glycol chlorohydrin or glycerol chlorohydrin.

Such compounds are sold, for example, under the names Dehyquart® by the company Henkel, Stepanquat® by the company Stepan, Noxamium® by the company CECA or Rewoquat® WE 18 by the company Rewo-Witco.

The composition according to the invention preferably contains a mixture of quaternary ammonium salts of mono-, di- and triesters with a weight majority of diester salts.

Examples of mixtures of ammonium salts that may be used include the mixture containing 15% to 30% by weight of acyloxyethyldihydroxyethylmethylammonium methyl sulfate, 45% to 60% of diacyloxyethylhydroxyethylmethylammonium methyl sulfate and 15% to 30% of triacyloxyethylmethylammonium methyl sulfate, the acyl radicals containing from 14 to 18 carbon atoms and being derived from palm oil that is optionally partially hydrogenated.

It is also possible to use the ammonium salts containing at least one ester function that are described in U.S. Pat. No. 4,874,554 and U.S. Pat. No. 4,137,180.

Among the quaternary ammonium salts of formula (I), the ones preferably used are, on the one hand, tetraalkylammonium chlorides, for instance dialkyldimethylammonium chlorides or alkyltrimethylammonium chlorides, in which the alkyl radical comprises from about 12 to 22 carbon atoms, in particular behenyl-trimethylammonium chloride, distearyldimethylammonium chloride, cetyltrimethyl-ammonium chloride, or benzyldimethylstearylammonium chloride, or, on the other hand, distearoylethylhydroxyethylmethylammonium methosulfate, dipalmitoylethylhydroxyethylammonium methosulfate or distearoylethylhydroxyethylammonium methosulfate, or else, finally, palmitylamido-propyltrimethylammonium chloride or stearamidopropyldimethyl(myristyl acetate)-ammonium chloride sold under the name Ceraphyl® 70 by the company Van Dyk.

Among all the cationic surfactants that may be present in the composition according to the invention, cationic surfactants from among cetyltrimethylammonium (INCI: cetrimonium-), behenyltrimethylammonium (INCI: behentrimonium-), dipalmitoylethylhydroxyethylmethylammonium, distearoylethylhydroxyethylmethyl-ammonium, methyl(C9-C19)alkyl(C10-C20)alkylamidoethylimidazolium and stearamidopropyldimethylamine salts (chloride or methosulfate), and the stearamidopropyldimethylammonium salt, and mixtures thereof, are preferably chosen.

The composition of the invention preferably comprises from 0.1% to 10% by weight, in particular from 0.5% to 8% by weight and better still from 1% to 5% by weight of cationic surfactants relative to the total weight of the composition.

The composition according to the invention may also comprise at least one silicone.

The silicone(s) that may be present in the composition according to the invention are in particular polyorganosiloxanes that may be in the form of aqueous solutions, i.e. dissolved, or optionally in the form of dispersions or microdispersions, or of aqueous emulsions. The polyorganosiloxanes may also be in the form of oils, waxes, resins or gums.

Organopolysiloxanes are defined in greater detail in Walter Noll's Chemistry and Technology of Silicones (1968), Academic Press.

The silicones may be volatile or non-volatile.

When they are volatile, the silicones are more particularly chosen from those with a boiling point of between 60° C. and 260° C., and even more particularly from:

(i) cyclic silicones comprising from 3 to 7 and preferably 4 to 5 silicon atoms.

These are, for example, octamethylcyclotetrasiloxane sold especially under the name Volatile Silicone 7207 by Union Carbide or Silbione 70045 V 2 by Rhône-Poulenc, decamethylcyclopentasiloxane sold under the name Volatile Silicone 7158 by Union Carbide, and Silbione 70045 V 5 by Rhône-Poulenc, and mixtures thereof.

Mention may also be made of cyclocopolymers of the dimethylsiloxane/methylalkylsiloxane type, such as Volatile Silicone FZ 3109 sold by the company Union Carbide, of chemical structure:

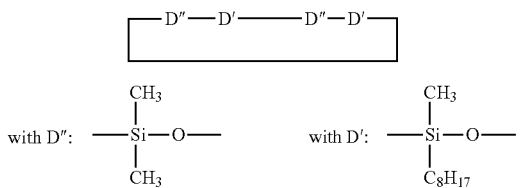

Mention may also be made of mixtures of cyclic silicones with organosilicon compounds, such as the mixture of octamethylcyclotetrasiloxane and tetrakis(trimethylsilyl)pentaerythritol (50/50) and the mixture of octamethylcyclotetrasiloxane and oxy-1,1'-bis(2,2,2',2',3,3'-hexatrimethylsilyloxy)neopentane;

(ii) linear volatile silicones containing 2 to 9 silicon atoms and having a viscosity of less than or equal to $5 \times 10^{-6}$ m2/s at 25° C. An example is decamethyltetrasiloxane sold especially under the name SH 200 by the company Toray Silicone. Silicones belonging to this category are also described in the article published in Cosmetics and Toiletries, Vol. 91, January 76, pp. 27-32, Todd & Byers Volatile Silicone Fluids for Cosmetics.

Non-volatile silicones and more particularly polyalkylsiloxanes, polyarylsiloxanes, polyalkylarylsiloxanes, silicone gums and resins, and polyorganosiloxanes modified with organofunctional groups, and mixtures thereof, are preferably used.

These silicones are more particularly chosen from polyalkylsiloxanes, among which mention may be made mainly of polydimethylsiloxanes containing trimethylsilyl end groups (Dimethicone according to the CTFA name) having a viscosity of from $5 \times 10^{-6}$ to 2.5 m2/s at 25° C. and preferably $1 \times 10^{-5}$ to 1 m2/s. The viscosity of the silicones is measured, for example, at 25° C. according to standard ASTM 445 Appendix C.

Among these polyalkylsiloxanes, mention may be made, in a non-limiting manner, of the following commercial products:

the Silbione oils of the 47 and 70 047 series or the Mirasil oils sold by Rhône-Poulenc, for instance the oil 70 047 V 500 000;

the oils of the Mirasil series sold by the company Rhône-Poulenc;

the oils of the 200 series from the company Dow Corning, such as, more particularly, DC200 with a viscosity of 60 000 cSt (centistokes);

the Viscasil oils from General Electric and certain oils of the SF series (SF 96, SF 18) from General Electric.

Mention may also be made of polydimethylsiloxanes containing dimethylsilanol end groups (Dimethiconol according to the CTFA name) such as the oils of the 48 series from the company Rhône-Poulenc.

Mention may also be made of polydimethylsiloxanes containing aminoethyl aminopropyl and α,Ω-silanol groups.

In this category of polyalkylsiloxanes, mention may also be made of the products sold under the names Abil Wax 9800 and 9801 by the company Goldschmidt, which are poly(C1-C20)alkylsiloxanes.

The polyalkylarylsiloxanes are particularly chosen from linear and/or branched polydimethyl methylphenylsiloxanes and polydimethyl diphenylsiloxanes with a viscosity of from $1 \times 10^{-5}$ to $5 \times 10^{-2}$ m2/s at 25° C.

Among these polyalkylarylsiloxanes, examples that may be mentioned include the products sold under the following names:

the Silbione oils of the 70 641 series from Rhône-Poulenc;
the oils of the Rhodorsil 70 633 and 763 series from Rhône-Poulenc;
the oil Dow Corning 556 Cosmetic Grade Fluid from Dow Corning;
the silicones of the PK series from Bayer, such as the product PK20;
the silicones of the series PN and PH from Bayer, such as the products PN1000 and PH 1000;
certain oils of the SF series from General Electric, such as SF 1023, SF 1154, SF 1250 and SF 1265.

The silicone gums that may be present in the composition according to the invention are especially polydiorganosiloxanes having high number-average molecular masses of between 200 000 and 1 000 000, used alone or as a mixture in a solvent. This solvent may be chosen from volatile silicones, polydimethylsiloxane (PDMS) oils, polyphenylmethylsiloxane (PPMS) oils, isoparaffins, polyisobutylenes, methylene chloride, pentane, dodecane and tridecanes, or mixtures thereof.

Mention may be made more particularly of the following products:
polydimethylsiloxane gums,
polydimethylsiloxane/methylvinylsiloxane gums,
poly[(dimethylsiloxane)/(vinylhydrogenosiloxane)] gums,
poly[(dimethylsiloxane)/(divinyldihydrogenosiloxane)] gums,
polydimethylsiloxane/diphenylsiloxane gums,
polydimethylsiloxane/phenylmethylsiloxane gums,
polydimethylsiloxane/diphenylsiloxane/methylvinylsiloxane gums.

Products that may be used more particularly are the following mixtures:
mixtures formed from a polydimethylsiloxane hydroxylated at the end of the chain (known as dimethiconol according to the nomenclature of the CTFA dictionary) and from a cyclic polydimethylsiloxane (known as cyclomethicone according to the nomenclature of the CTFA dictionary), such as the product Q2 1401 sold by the company Dow Corning;
mixtures formed from a polydimethylsiloxane gum with a cyclic silicone, such as the product SF 1214 Silicone Fluid from the company General Electric, this product being an SF 30 gum corresponding to a dimethicone, having a number-average molecular weight of 500 000, dissolved in the oil SF 1202 Silicone Fluid corresponding to decamethylcyclopentasiloxane;
mixtures of two PDMSs of different viscosities, and more particularly of a PDMS gum and a PDMS oil, such as the product SF 1236 from the company General Electric. The product SF 1236 is a mixture of an SE 30 gum defined above, with a viscosity of 20 m2/s, and of an SF 96 oil with a viscosity of 5×10-6 m2/s. This product preferably comprises 15% by weight of SE 30 gum and 85% by weight of an SF 96 oil.

The organopolysiloxane resins that may be present in the composition according to the invention are crosslinked siloxane systems containing the following units: R2SiO2/2, R3SiO1/2, RSiO3/2 and SiO4/2 in which R represents a hydrocarbon group containing 1 to 16 carbon atoms or a phenyl group. Among these products, those particularly preferred are the ones in which R denotes a C1-C4 lower alkyl radical, more particularly methyl, or a phenyl radical.

Among these resins, mention may be made of the product sold under the name Dow Corning 593 or those sold under the names Silicone Fluid SS 4230 and SS 4267 by the company General Electric, which are silicones of dimethyl/trimethyl siloxane structure.

Mention may also be made of the trimethyl siloxysilicate type resins sold especially under the names X22-4914, X21-5034 and X21-5037 by the company Shin-Etsu.

The organomodified silicones that may be present in the composition according to the invention are silicones as defined above and comprising in their structure one or more organofunctional groups attached via a hydrocarbon-based radical.

Among the organomodified silicones, mention may be made of polyorganosiloxanes comprising:
polyethylencoxy and/or polypropyleneoxy groups optionally comprising C6-C24 alkyl groups, such as the oxyethylenated and oxypropylenated poly(methyllauryl/methylsiloxane) sold under the name Dow Corning 5200 Formulation Aid by the company Dow Corning (INCI: Lauryl PEG/PPG-18/18 methicone), the products known as dimethicone copolyol sold by the company Dow Corning under the name DC 1248 or the oils Silwet L 722, L 7500, L 77 and L 711 by the company Union Carbide, and the (C12)alkylmethicone copolyol sold by the company Dow Corning under the name Q2 5200;
thiol groups, such as the products sold under the names GP 72 A and GP 71 from Genesee;
alkoxylated groups, such as the product sold under the name Silicone Copolymer F-755 by SWS Silicones and Abil Wax 2428, 2434 and 2440 by the company Goldschmidt;
hydroxylated groups, such as the polyorganosiloxanes containing a hydroxyalkyl function, described in French patent application FR-A-85/16334;
acyloxyalkyl groups, for instance the polyorganosiloxanes described in U.S. Pat. No. 4,957,732;
anionic groups of the phosphate or carboxylic acid type, for instance in the products described in patent EP 186 507 from the company Chisso Corporation, or of the alkylcarboxylic type, such as those present in the product X-22-3701E from the company Shin-Etsu; 2-hydroxyalkyl sulfonate; 2-hydroxyalkyl thiosulfate such as the products sold by the company Goldschmidt under the names Abil S201 and Abil S255;
hydroxyacylamino groups, such as the polyorganosiloxanes described in patent application EP 342 834. Mention may be made, for example, of the product Q2-8413 from the company Dow Corning.

Among the organomodified silicones, mention may also be made of amino silicones.

The term "amino silicone" means any polyaminosiloxane, i.e. any polysiloxane comprising at least one primary, secondary or tertiary amine function or a quaternary ammonium group.

Preferably, the amino silicone(s) used in the cosmetic composition according to the present invention are chosen from:
(a) the compounds corresponding to formula (V) below:

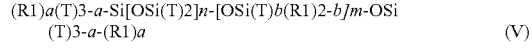

in which:
T is a hydrogen atom or a phenyl, hydroxyl (—OH) or C1-C8 alkyl radical, and preferably methyl, or a C1-C8 alkoxy, preferably methoxy,
a denotes the number 0 or an integer from 1 to 3, and preferably 0,
b denotes 0 or 1, and in particular 1, m and n are numbers such that the sum (n+m) can range especially from 1 to 2000 and in particular from 50 to 150, n possibly denoting a number from 0 to 1999 and especially from 49 to 149, and m possibly denoting a number from 1 to 2000 and especially from 1 to 10;

R1 is a monovalent radical of formula -CqH2qL in which q is a number from 2 to 8 and L is an optionally quaternized amino group chosen from the following groups:
—N(R2)-CH2-CH2-N(R2)2;
—N(R2)2;
—N+(R2)3Q-;
—N+(R2)(H)2Q-;
—N+(R2)2HQ-;
—N(R2)-CH2-CH2-N+(R2)(H)2Q-, in which R2 can denote a hydrogen atom, a phenyl, a benzyl or a saturated monovalent hydrocarbon-based radical, for example a C1-C20 alkyl radical, and Q- represents a halide ion such as, for example, fluoride, chloride, bromide or iodide.

In particular, the amino silicones corresponding to the definition of formula (V) are chosen from the compounds corresponding to formula (VI) below:

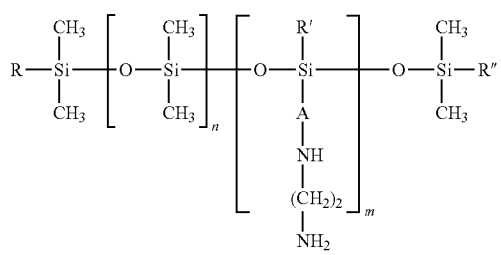

(VI)

in which R, R' and R", which may be identical or different, denote a C1-C4 alkyl radical, preferably CH3; a C1-C4 alkoxy radical, preferably methoxy; or OH; A represents a linear or branched, C3-C8 and preferably C3-C6 alkylene radical; m and n are integers dependent on the molecular weight and whose sum is between 1 and 2000.

According to a first possibility, R, R' and R", which may be identical or different, represent a C1-C4 alkyl or hydroxyl radical, A represents a C3 alkylene radical and m and n are such that the weight-average molecular mass of the compound is between 5000 and 500 000 approximately. Compounds of this type are referred to in the CTFA dictionary as "amodimethicones".

According to a second possibility, R, R' and R", which may be identical or different, represent a C1-C4 alkoxy or hydroxyl radical, at least one of the radicals R or R" is an alkoxy radical and A represents a C3 alkylene radical. The hydroxyl/alkoxy mole ratio is preferably between 0.2/1 and 0.4/1 and advantageously equal to 0.3/1. Moreover, m and n are such that the weight-average molecular mass of the compound is between 2000 and 106. More particularly, n is between 0 and 999 and m is between 1 and 1000, the sum of n and m being between 1 and 1000.

In this category of compounds, mention may be made, inter alia, of the product Belsil® ADM 652 sold by Wacker.

According to a third possibility, R and R", which are different, represent a C1-C4 alkoxy or hydroxyl radical, at least one of the radicals R or R" is an alkoxy radical, R' represents a methyl radical and A represents a C3 alkylene radical. The hydroxyl/alkoxy mole ratio is preferably between 1/0.8 and 1/1.1 and is advantageously equal to 1/0.95. Moreover, m and n are such that the weight-average molecular mass of the compound is between 2000 and 200 000. More particularly, n is between 0 and 999 and m is between 1 and 1000, the sum of n and m being between 1 and 1000.

More particularly, mention may be made of the product Fluid WR® 1300 sold by Wacker.

According to a fourth possibility, R and R" represent a hydroxyl radical, R' represents a methyl radical and A is a C4-C8 and preferably C4 alkylene radical. Moreover, m and n are such that the weight-average molecular mass of the compound is between 2000 and 106. More particularly, n is between 0 and 1999 and m is between 1 and 2000, the sum of n and m being between 1 and 2000.

A product of this type is especially sold under the name DC28299 by Dow Corning.

It should be noted that the molecular mass of these silicones is determined by gel permeation chromatography (ambient temperature, polystyrene standard; μ styragem columns; eluent THF; flow rate 1 mm/m; 200 μl of a solution containing 0.5% by weight of silicone are injected into THF and detection is performed by refractometry and UV-metry).

A product corresponding to the definition of formula (V) is in particular the polymer known in the CTFA dictionary (7th edition, 1997) as "trimethylsilyl amodimethicone", corresponding to formula (VII) below:

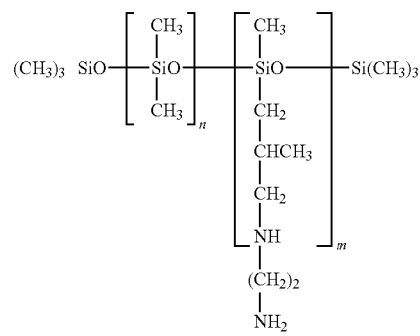

(VII)

in which n and m have the meanings given above in accordance with formula (V) or (VI).

Such compounds are described, for example, in EP 0 095 238; a compound of formula (VII) is sold, for example, under the name Q2-8220 by the company OSI.

(b) the compounds corresponding to formula (VIII) below:

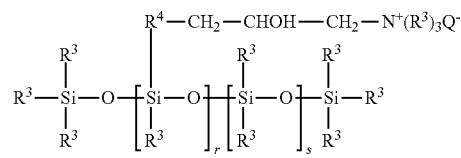

(VIII)

in which:
R3 represents a monovalent C1-C18 hydrocarbon-based radical, and in particular a C1-C18 alkyl or C2-C18 alkenyl radical, for example methyl;
R4 represents a divalent hydrocarbon-based radical, especially a C1-C18 alkylene radical or a divalent C1-C18, and for example C1-C8, alkyleneoxy radical;
Q- is a halide ion, especially chloride;

r represents an average statistical value from 2 to 20 and in particular from 2 to 8;

s represents an average statistical value from 20 to 200 and in particular from 20 to 50.

Such compounds are described more particularly in U.S. Pat. No. 4,185,087.

A compound falling within this class is the product sold by the company Union Carbide under the name Ucar Silicone ALE 56.

(c) the quaternary ammonium silicones of formula (IX):

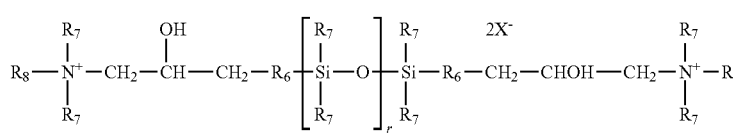

in which:

R7, which may be identical or different, represent a monovalent hydrocarbon-based radical containing from 1 to 18 carbon atoms, and in particular a C1-C18 alkyl radical, a C2-C18 alkenyl radical or a ring comprising 5 or 6 carbon atoms, for example methyl;

R6 represents a divalent hydrocarbon-based radical, especially a C1-C18 alkylene radical or a divalent C1-C18, for example C1-C8, alkyleneoxy radical linked to the Si via an SiC bond;

R8, which may be identical or different, represent a hydrogen atom, a monovalent hydrocarbon-based radical containing from 1 to 18 carbon atoms, and in particular a C1-C18 alkyl radical, a C2-C18 alkenyl radical or a radical —R6-NHCOR7;

X— is an anion such as a halide ion, especially chloride, or an organic acid salt (acetate, etc.);

r represents a mean statistical value from 2 to 200 and in particular from 5 to 100.

These silicones are described, for example, in patent application EP-A-0 530 974.

(d) the amino silicones of the following formula:

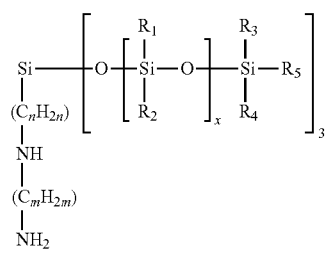

in which:

R1, R2, R3 and R4, which may be identical or different, denote a C1-C4 alkyl radical or a phenyl group, R5 denotes a C1-C4 alkyl radical or a hydroxyl group, n is an integer ranging from 1 to 5, m is an integer ranging from 1 to 5, and in which x is chosen such that the amine number is between 0.01 and 1 meq./g.

The silicone(s) that are particularly preferred are polysiloxanes containing amine groups, such as the silicones of formula (VI) or the silicones of formula (VII), and even more particularly silicones containing quaternary ammonium groups such as the silicones of formula (IX).

When these compounds are used, one particularly advantageous embodiment involves their joint use with cationic and/or nonionic surfactants.

By way of example, use may be made of the product sold under the name Cationic Emulsion DC 929 by the company Dow Corning, which comprises, besides amodimethicone, a cationic surfactant comprising a mixture of products corresponding to formula (X):

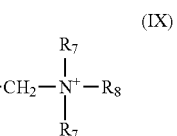

in which R5 denotes C14-C22 alkenyl and/or alkyl radicals derived from tallow fatty acids, and known under the CTFA name tallowtrimonium chloride, in combination with a nonionic surfactant of formula:

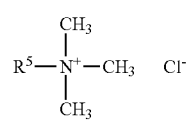

C9H19-C6H4-(OC2H4)10-OH, known under the CTFA name Nonoxynol 10.

By way of example, use may be made of the product sold under the name Cationic Emulsion DC 939 by the company Dow Corning, which comprises, besides amodimethicone, a cationic surfactant which is trimethylcetylammonium chloride and a nonionic surfactant of formula: C13H27-(OC2H4)12-OH, known under the CTFA name Trideceth-12.

Another commercial product that may be used according to the invention is the product sold under the name Dow Corning Q2 7224 by the company Dow Corning, comprising, in combination, the trimethylsilyl amodimethicone of formula (C) described above, a nonionic surfactant of formula: C8H17-C6H4-(OCH2CH2)40-OH, known under the CTFA name Octoxynol-40, a second nonionic surfactant of formula: C12H25-(OCH2-CH2)6-OH, known under the CTFA name Isolaureth-6, and propylene glycol.

Among all the silicones that may be present in the composition according to the invention, it is preferred to choose silicone(s) from among non-volatile silicones and more particularly polyalkylsiloxanes, polyarylsiloxanes, polyalkylarylsiloxanes, silicone gums, polyorganosiloxanes modified with organofunctional groups chosen from amino silicones, and silicones comprising polyethyleneoxy and/or polypropyleneoxy groups, and also mixtures thereof.

More preferably, the silicone(s) are chosen from polydimethylsiloxanes optionally in the form of gums, poly[(dimethylsiloxane)(vinylhydrogenosiloxane)] gums, polyorganosiloxanes modified with organofunctional groups and chosen from amino silicones, and silicones comprising polyethyleneoxy and/or polypropyleneoxy groups, and also mixtures thereof.

When the composition according to the invention comprises at least one silicone, the silicone(s) generally represent(s) from 0.5% to 20% and preferably from 0.1% to 10% by weight relative to the total weight of the composition.

The composition according to the invention may also comprise one or more C8-C40 fatty alcohols.

The C8-C40 fatty alcohols may be chosen from alcohols of formula R'OH, in which R' denotes a saturated or unsaturated, linear or branched radical, comprising from 8 to 40 carbon atoms and preferably 8 to 30 carbon atoms. R' preferably denotes a C12-C24 alkyl or C12-C24 alkenyl group. R' may be substituted with one or more hydroxyl groups.

The fatty alcohol(s) may be chosen in particular from lauryl alcohol, cetyl alcohol, dodecyl alcohol, decyl alcohol, stearyl alcohol, oleyl alcohol, behenyl alcohol, linoleyl alcohol, undecylenyl alcohol, palmitoleyl alcohol, arachidonyl alcohol, myristyl alcohol and erucyl alcohol. A mixture of fatty alcohols may also be used, which means that several species of fatty alcohols may coexist in a commercial product, in the form of a mixture. Mixtures of fatty alcohols that may be mentioned include cetylstearyl alcohol and cetearyl alcohol.

Preferably, the fatty alcohol(s) are chosen from myristyl alcohol, cetyl alcohol and stearyl alcohol, and mixtures thereof.

When the composition according to the invention comprises at least one fatty alcohol, the fatty alcohol(s) generally represent from 0.5% to 25% and preferably from 1% to 10% by weight relative to the total weight of the composition.

The composition according to the invention may also comprise one or more cationic polymers.

For the purposes of the present invention, the term "cationic polymer" means any polymer comprising cationic groups and/or groups that may be ionized into cationic groups.

The cationic polymers that may be used in the cosmetic composition according to the invention are preferably chosen from polymers comprising primary, secondary, tertiary and/or quaternary amine groups forming part of the polymer chain or directly attached thereto, and having a number average molecular mass of between 500 and about 5 000 000 and preferably between 1000 and 3 000 000.

Among these polymers, mention may be made more particularly of the following cationic polymers:

(1) homopolymers or copolymers of acrylic or methacrylic esters or amides with amine functions, and comprising at least one of the units of the following formulae:

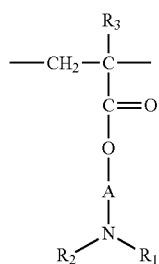

(A)

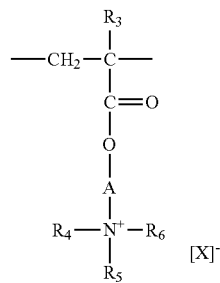

(B)

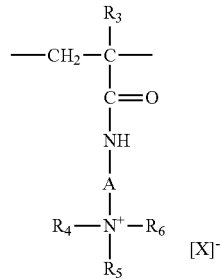

(C)

in which:

R1 and R2, which may be identical or different, each represent a hydrogen atom or an alkyl group having from 1 to 6 carbon atoms;

R3 denotes a hydrogen atom or a group CH3;

A is a linear or branched alkyl group comprising from 1 to 6 carbon atoms or a hydroxyalkyl group comprising from 1 to 4 carbon atoms;

R4, R5 and R6, which may be identical or different, represent an alkyl group having from 1 to 18 carbon atoms or a benzyl group;

X— denotes a methosulfate anion or a halide such as chloride or bromide.

The copolymers of the family (1) also contain one or more comonomer units that may be chosen from the family of acrylamides, methacrylamides, diacetone acrylamides, acrylamides and methacrylamides substituted on the nitrogen with lower (C1-4) alkyl groups, groups derived from acrylic or methacrylic acids or esters thereof, vinyllactams such as vinylpyrrolidone or vinylcaprolactam, and vinyl esters.

Thus, among these copolymers of the family (1), mention may be made of:

copolymers of acrylamide and of dimethylaminoethyl methacrylate quaternized with dimethyl sulfate or with a dimethyl halide, such as the product sold under the name Hercofloc® by the company Hercules, copolymers of acrylamide and of methacryloyloxyethyltrimethylammonium chloride, described, for example, in patent application EP-A-080 976 and sold under the name Bina Quat P 100 by the company Ciba Geigy, copolymers of acrylamide and of methacryloyloxyethyltrimethylammonium methosulfate, such as the product sold under the name Reten by the company Hercules, quaternized or non-quaternized vinylpyrrolidone/dialkylaminoalkyl acrylate or methacrylate copolymers, such as the products sold under the name Gafquat® by the company ISP, for instance Gafquat® 734 or Gafquat® 755, or alternatively the products known as Copolymer® 845, 958 and 937. These polymers are described in detail in French patents 2 077 143 and 2 393 573, dimethylaminoethyl methacrylate/vinylcaprolactam/vinylpyrrolidone terpolymers, such as the product sold under the name Gaffix® VC 713 by the company ISP, and quaternized vinylpyrrolidone/dimethylaminopropylmethacrylamide copolymers, especially such as the product sold under the name Gafquat® HS100 by the company ISP;

crosslinked polymers of methacryloyloxy(C1-C4)alkyltri(C1-C4)alkylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with an olefinically unsaturated compound, in particular methylenebisacrylamide. A crosslinked acrylamide/methacryloyl-oxyethyltrimethylammonium chloride copolymer (20/80 by weight) in the form of a dispersion containing 50% by weight of the copolymer in mineral oil can be used more particularly. This dispersion is sold under the name Salcare® SC 92 by the company Ciba. A crosslinked methacryloyloxyethyltrimethylammonium chloride homopolymer containing about 50% by weight of the homopolymer in mineral oil or in a liquid ester can also be used. These dispersions are sold under the names Salcare® SC 95 and Salcare® SC 96 by the company Ciba.

(2) cationic polysaccharides, and in particular those chosen from:

a) cellulose ether derivatives comprising quaternary ammonium groups, described in patent FR 1 492 597. These polymers are also defined in the CTFA dictionary as quaternary ammoniums of hydroxyethylcellulose that has reacted with an epoxide substituted with a trimethylammonium group;

b) cellulose derivatives grafted with a water-soluble monomer comprising a quaternary ammonium, and described especially in U.S. Pat. No. 4,131,576, such as hydroxyalkylcelluloses, for instance hydroxymethyl, hydroxyethyl or hydroxypropyl celluloses grafted especially with a methacryloylethyltrimethylammonium, methacryl-amidopropyltrimethylammonium or dimethyldiallylammonium salt.

The commercial products corresponding to this definition are more particularly the products sold under the names Celquat L 200 and Celquat H 100 by the company National Starch.

c) cationic polygalactomannans such as those described in U.S. Pat. Nos. 3,589,578 and 4,031,307, such as guar gums containing cationic trialkylammonium groups. Such products are sold especially under the trade names Jaguar C13 S, Jaguar C 15 and Jaguar C 17 by the company Rhodia.

(3) quaternary copolymers of vinylpyrrolidone and of vinylimidazole.

(4) chitosans or salts thereof; the salts that can be used are, in particular, chitosan acetate, lactate, glutamate, gluconate or pyrrolidonecarboxylate.

Among these compounds, mention may be made of chitosan having a degree of deacetylation of 90.5% by weight, sold under the name Kytan Brut Standard by the company Aber Technologies, and chitosan pyrrolidonecarboxylate sold under the name Kytamer® PC by the company Amerchol.

Among all the cationic polymers that may be present in the composition according to the invention, the cationic polymer(s) are preferably chosen from crosslinked polymers of methacryloyloxy(C1-C4)alkyltri(C1-C4)alkylammonium salts.

When the composition comprises at least one cationic polymer, this or these polymer(s) are present in a concentration preferably ranging from 0.1% to 10% by weight relative to the total weight of the composition.

The composition according to the invention comprises a cosmetically acceptable medium.

The cosmetically acceptable medium is formed from water or from a mixture of water and of at least one cosmetically acceptable solvent preferably chosen from C1-C4 lower alcohols, such as ethanol, isopropanol, tert-butanol or n-butanol; polyols such as glycerol, propylene glycol and polyethylene glycols; and mixtures thereof.

The composition according to the invention may also comprise one or more standard additives that are well known in the art, other than the compounds defined previously. As examples of additives that may be used according to the invention, mention may be made of ionic or nonionic associative or non-associative polymers, silanes, anionic surfactants, amphoteric or zwitterionic surfactants, nonionic surfactants, proteins, vitamins, reducing agents, plasticizers, softeners, antifoams, moisturizers, pigments, clays, mineral fillers, UV-screening agents, mineral colloids, peptizers, solubilizers, fragrances, preserving agents, nacreous agents, propellants and mineral or organic thickeners; these additives being different from the compounds defined hereinabove.

A person skilled in the art will take care to select the optional additive(s) and the amount thereof such that they do not harm the properties of the compositions of the present invention.

The additive(s) are generally present in the composition according to the invention in an amount ranging from 0 to 20% by weight relative to the total weight of the composition.

The compositions according to the invention may be in the form of a rinse-out or leave-in care composition, these compositions being in the form of a more or less thickened lotion, a cream, a gel or an emulsion.

Another subject of the invention is the use of the cosmetic composition as described above for the cosmetic treatment of keratin materials, preferably keratin fibres such as the hair, and especially as a rinse-out haircare product.

The invention also relates to a cosmetic process for treating keratin materials, preferably keratin fibres such as the hair, which comprises the application of an effective amount of a cosmetic composition as described above to the materials, and optional rinsing of the composition after an optional leave-on time.

When the composition according to the invention is applied in the form of a lotion or a cream, it is optionally left to stand on the hair for about 0.5 to 5 minutes, and is then optionally rinsed out with water.

The examples that follow are given as illustrations of the present invention.

In the examples that follow, all the amounts are indicated as weight percentages relative to the total weight of the composition, unless otherwise indicated.

EXAMPLES

The rinse-out care compositions A, B and C below were prepared from the ingredients indicated in the table below.

|  | Compositions | | |
| --- | --- | --- | --- |
|  | A | B | C |
| Mixture mainly composed of pure n-undecane and n-tridecane according to example 2 of patent application WO 2008/155 059 | 5 | 3 | — |
| Mixture of n-dodecane and n-tetradecane (Vegelight 1214 - Biosynthis) | — | — | 5 |
| Copolymer of polydimethylsiloxane containing α,Ω-vinyl groups/α,Ω-hydrogenopolysiloxane at 67% by weight of active material in a cationic emulsion containing 2.2% by weight of cetyl trimethyl ammonium chloride (Dow Corning 2 1997 Cationic Emulsion - Dow Corning) | 2 (1.34% AM) | 2 (1.34% AM) | 2 (1.34% AM) |
| Myristyl alcohol (Nacol 14-98 - Sasol) | 3 | 3 | 3 |
| Cetyl alcohol (Nacol 16-98 - Sasol) | 1 | 1 | 1 |
| Crosslinked ethyltrimethylammonium methacrylate chloride homopolymer, as an inverse emulsion at 50% by weight in a mineral oil (Salcare ® SC 95 - Ciba) | 0.5 (0.25% AM) | 0.5 (0.25% AM) | 0.5 (0.25% AM) |
| Stearylamidopropyldimethylamine (Mackine 301 - Rhodia) | 2.5 | 2.5 | 2.5 |
| Distearoylethylhydroxyethylmethylammonium methosulfate at 75% by weight in cetylstearyl alcohol (Dehyquart F75 - Cognis) | 2.5 (1.875% AM) | 2.5 (1.875% AM) | 2.5 (1.875% AM) |
| Lauryl PEG/PPG-18/18 methicone at 72% by weight of active material (Dow Corning 5200 Formulation Aid - Dow Corning) | 1 (0.72% AM) | 1 (0.72% AM) | 1 (0.72% AM) |
| Citric acid monohydrate | 0.85 | 0.85 | 0.85 |
| Preserving agent, fragrance | qs | qs | qs |
| Deionized water | qs 100 | qs 100 | qs 100 |
| Weight ratio of the amount of volatile linear alkanes to the amount of cationic surfactants | 1.13 | 0.68 | 1.13 |

% AM: percentage by weight of Active Material relative to the total weight of the composition It is observed that compositions A, B and C according to the invention lead to good smoothing of the hair fibre during rinsing and on dried hair.

The above written description of the invention provides a manner and process of making and using it such that any person skilled in this art is enabled to make and use the same, this enablement being provided in particular for the subject matter of the appended claims, which make up a part of the original description.

As used herein, the words "a" and "an" and the like carry the meaning of "one or more."

The phrases "selected from the group consisting of," "chosen from," and the like include mixtures of the specified materials. Terms such as "contain(s)" and the like are open terms meaning 'including at least' unless otherwise specifically noted.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The invention claimed is:

1. A composition comprising, in a cosmetically acceptable medium:
   (a) 3 to 10% by weight of relative to the total weight of the composition of a mixture comprising undecane and tridecane; or dodecane and tetradecane, and
   (b) 1 to 5% by weight relative to the total weight of the composition of a cationic surfactant selected from the group consisting of behenyl-trimethylammonium chloride, distearyl dimethylammonium chloride, cetyl trimethyl ammonium chloride, or benzyl dimethyl stearylammonium chloride, distearoylethylhydroxyethylmethylammonium methosulfate, dipalmitoylethylhydroxyethylammonium methosulfate, distearoylethylhydroxyethylammonium methosulfate, palmitylamido propyltrimethylammonium chloride and stearamidopropyldimethyl(myristyl acetate)-ammonium chloride
(c) from 0.1 to 10% by weight relative to the total weight of the composition of cationic polymer that is a crosslinked polymer of methacryloyloxy(C1-C4)alkyltri(C1-C4)alkylammonium salt
(d) the weight ratio of the amount of volatile linear alkane(s) to the amount of cationic surfactant(s) 0.1 to 1.4.

2. The composition according to claim 1, further comprising at least one silicone and/or at least one C8-C40 fatty alcohol.

3. The composition according to claim 1, further comprising at least one additive chosen from ionic or nonionic associative or non-associative polymers, silanes, anionic surfactants, amphoteric or zwitterionic surfactants, nonionic surfactants, proteins, vitamins, reducing agents, plasticizers, softeners, antifoams, moisturizers, pigments, clays, mineral fillers, UV-screening agents, mineral colloids, peptizers, solubilizers, fragrances, preserving agents, nacreous agents, propellants and mineral or organic thickeners.

4. A method for treating hair, comprising applying the composition according to claim 1 to the hair.

* * * * *